(12) United States Patent
Hamilton

(10) Patent No.: US 6,335,361 B1
(45) Date of Patent: Jan. 1, 2002

(54) METHOD OF TREATING BENIGN FORGETFULNESS

(75) Inventor: Nathan D. Hamilton, Palo Alto, CA (US)

(73) Assignee: Juvenon Inc., Orinda, CA (US)

( * ) Notice: Subject to any disclaimer, the term of this patent is extended or adjusted under 35 U.S.C. 154(b) by 0 days.

(21) Appl. No.: 09/706,207

(22) Filed: Nov. 2, 2000

Related U.S. Application Data

(60) Provisional application No. 60/163,352, filed on Nov. 3, 1999, and provisional application No. 60/223,167, filed on Aug. 7, 2000.

(51) Int. Cl.$^7$ .............. A61K 31/385; A61K 31/205; A61K 31/195; A61K 31/12

(52) U.S. Cl. .............. 514/440; 514/556; 514/565; 514/689

(58) Field of Search .............. 514/440, 556, 514/565, 689

(56) References Cited

U.S. PATENT DOCUMENTS

| | | | |
|---|---|---|---|
| 4,401,827 A | 8/1983 | de Witt | 560/1 |
| 4,599,232 A | 7/1986 | Bertelli | 424/94 |
| 4,859,698 A | 8/1989 | Cavarra et al. | 514/445 |
| 5,240,961 A | 8/1993 | Shug | 514/556 |
| 5,260,464 A | 11/1993 | Della Valle et al. | 554/80 |
| 5,391,550 A | 2/1995 | Carniglia et al. | 514/23 |
| 5,916,912 A | 6/1999 | Ames et al. | 514/440 |

OTHER PUBLICATIONS

R. Stewart and D. Liolitsa: Type 2 diabetes mellitus, cognitive impairment and dementia: Diabetic Medicine 1999, 16, 93–112.

Salmon E, Van der Linden M, Collette F, Delfiore G, Maquet P, Degueldre C, Luxen A, Franck G:Regional brain activity during working memory tasks: Brain, 1996 Oct;119 (Pt 5): 1617–25. (Abstract).

Wright CE, Harding GF, Orwin A: The flash and pattern VEP as a diagnostic indicator of dementia: Doc Ophthalmol, 1986 Jan 31;62(1):89–96. (Abstract).

Petrie WM: Alzheimer's disease: Compr Ther 1985 Jul;11(7):38–43. (Abstract).

Cummings JL, Benson dF: Subcortial dementia. Review of an emerging concept: Arch Neurol 1984 Aug;41(41(8):874–9.

Milder DG, Elliott CF, Evans WA: Neuropathological findings in a case of coexistent progressive supranuclear palsy and Alzheimer's disease: Clin Exp Neurol: 1984;20:181–7. (Abstract).

Branconnier RJ, Cole JO, Spera KF, DeVitt DR: Recall and recognition as diagnostic indices of Malignant Memory Loss in Senile Dementia: a Bayesian analysis: Exp Aging Re, 1982 Fall–Winter;8(3–4):189–93. (Abstract).

Jolles, J, Verhey FR, Riedel WJ, Houx PJ: Cognitive impairment in elderly people. Predisposing factors and implications for experimental drug studies: Drugs Aging, 1995 Dec;7(6):459–79. (Abstract).

Gallai V, Mazzotta G, Del Gatto, Montesi S, Mazzetti A, Dominici P, Della Monica A: A clinical and neurophysiological trial on nootropic drugs in patients with mental decline: Acta Neurol (Napoli) 1991 Feb;13(1):1–12. (Abstract).

Bamford KA, Caine ED: Does "benign senescent forgetfulness" exist?: Clin Geriart Med, 1988 Nov;4(4):897–916. (Abstract).

Brayne C, Calloway P: Normal ageing, impaired cognitive function, and senile dementia of the Alzheimer's type: a continuum?: Lancet, 1988 Jun 4;1(8597):1265–7. (Abstract).

Eustache F, Rioux P, Desgranges B, Marchal G, Petti–Taboue MC, Dary M, Lechevalier B, Baron JC: Healthy aging, memory subsystems and regional cerebral oxygen consumption: Neuropsychologia, 1995 Jul;33(7):867–87. (Abstract).

Poser CM, Kassirer MR, Peyser JM: Benign encephalopathy of pregnancy. Preliminary clinical observations: Acat Neurol Scand, 1986 Jan;73(1):39–43. (Abstract).

Campbell BA, Sanances CB, Gaddy JR: Animal models of infantile amnesia, benign senescent forgetfulness, and senile dementia: Neurobehave Toxicol Teratol, 1984 Nov–Dec;6(6):467–71. (Abstract).

Ames, BN: Micronutrients prevent cancer and delay aging: TOxicol Lett, 1998 Dec 28;102–103: 5–18.

Mark K. Shigenaga, Tory M. Hagen, and Bruce N. Ames: Oxidative damage and mitochondiral decay in aging, Proc. Natl. Acad. Sci. USA, vol. 91, pp. 10771–10778 (No date Available).

Heinonen OJ; Takala J: Moderate carnitine depletion and long–chain fatty acid oxidation, exercise capacity, and nitrogen balance in the rat, Pediatr Res, 36(3):288–92 1994 Sep. (Abstract).

(List continued on next page.)

*Primary Examiner*—Raymond Henley, III
(74) *Attorney, Agent, or Firm*—Sierra Patent Group, Lt

(57) ABSTRACT

Disclosed herein are methods to treat cognition disorders, particularly those associated with aging. The method comprises administering a combination of a carnitine and an oxidant. Preferably the oxidant is thioctic acid. Preferably 0.12 grams to 3 grams of carnitine (particularly ALC) and 0.12 and 1.5 grams of R-α-lipoic acid are administered. Optionally, coenzyme Q and/or creatine also are administered. Preferably 10 mg to 500 mg/day of coenzyme Q10 and 1 to 30 grams/day of creatine are administered. The same method can be used to treat cognition deficits associated with carbon monoxide poisoning, mild traumatic brain injury, Type 2 diabetes mellitus, obsessive-compulsive disorder, environmental toxin exposure, and other conditions.

36 Claims, No Drawings

OTHER PUBLICATIONS

Sundlvist KE; Vuorinen KH; Peuhkurinen IE: Metabolic effects of propionate, hexanoate and propionylcarnitine in normoxa, ischaemia and reperfusion. Does an anaplerotic substrate protect the ischaemic myocardium?: Eur Heart J, 15(4):561–70 1994 Apr. (Abstract).

N'averi HK; Leinonen H; Kilavuori K; H'ark'onen M: Skeletal muscle lactate accumulation and creatine phosphate depletion during heavy exercise in congestive heart failure. Cause of limited exercise capacity? Eur Heart J, 18(12):1937–45 1997 Dec (Abstract).

Kagan T, Davis C, Lin L, Zakeri Z: Coenzyme Q10 can in some circumstances block apoptosis, and this effect is mediated through mitochondria. Ann NY Acad Sci, 1999;887:31–47.

Ravaglia G, Forti P, Maioli F, Bastagli L, Facchini A, Mariani E, Savarino L, Sassi C, Cucinotta D, Lenaz G: Effect of micronutrient status on natural killer cell immune function in healthy free–living subjects aged >/=90 y., Am J Clin Nutr 2000 Feb;71(2):590–8. (Abstract).

Turunen M, Appelkvist EL, Sindelar P, Dallner G: Blood concentration of coenzyme Q(10) increases in rata when esterfied forms are administered, J Nutr 1999 Dec;129(12):2113–8.

Tomasetti M, Littarru GP, Stocker R, Alleva R: Coenzyme Q10 enrichment decreases oxidative DNA damage in human lymphocytes, Free Radic Biol Med 1999 Nov;27(9–10):1027–32. (Abstract).

Overvad K, Diamant B, Holm L, Holmer G, Mortensen S: Coenzme Q10 in health and disease, Eur J Clin Nutr 1999 Oct;53(10):764–70. (Abstract).

Challem JJ: Toward a new definition of essential nutrients; is it now time for a third 'vitamin' paradigm?, Med Hypothes 1999 May;52(5):417–22. (Abstract).

Huertas, JR, Martinez–Velasco E, Ibanez S, Lopez–Frias M, Ochoa JJ, Quiles J, Parenti Castelli G, Mataix J, Lenaz G: Virgin olive oil and coenzyme Q10 protect heart mitochondria from peroxidative damage during aging, Biofactors 1999;9(2–4):337–43. (Abstract).

Loring DW, Levin HS, Papanicolaou AC, Larrabee GJ, Eisenberg HM: Auditory evoked potentials in senescent forgetfulness: Int J Neurosci, 1984 Oct;24(2):133–41. (Abstract).

Saleman M: Brain tumors in elderly patients: Am Fam Physician, 1983 Apr;27(4):137–43. (Abstract).

Hoyert DL, Rosenberg HM: Mortality from Alzheimer's disease: an update: Natl Vital Stat Rep, 1999 Jun 30;47(20):1–8. (Abstract).

Keady J, Gillard J, Evers C, Milton S: The DIAL–log study 1: profiling the experience of people with dementia: Br J Nurs, 1999 Mar 25–Apr 7;8(6):387–93. (Abstract).

Jolles J, Verhey FR, Riedel WJ, Houx PJ: Cognitive impairment in elderly people. Predisposing factors and implications for experimental drug studies: Drugs Aging, 1995 Dec;7(6):459–79. (Abstract).

Skelton WP 3d, Skelton NK: Alzheimer's disease. Recognizing and treating a frustrating condition: Postgrad Med, 1991 Sep 15;90(4):33–44, 37–41. (Abstract).

Martin RL, Gerteis G, Gavrielli WF Jr: A family–genetic study of dementia of Alzheimer type: Arch Gen Psychiatry, 1988 Oct;45(10):894–900. (Abstract).

Gottfries CG: Dementia: classification and aspects of treatment: Psychopharmacol Ser, 1988;5:187–95. (Abstract).

William Paul Skelton III, MD, Nadine Khouzan Skelton, MD: Alzheimer's disease. Recognizing and treating a frustrating condition: Postgraduate Medicine, 1991 Sept 15, vol. 90 No. 4. (Abstract).

Cassella AG, Department of CNS Pharmacology, Frankfurt, Federal Republic of Germany: Memory modulation with peripherally acting cholinergic drugs: Psychopharmacology (Berl) 1992;106(3):375–82. (Abstract).

Elrod K, Buccafusco JJ: Correlation of the amnestic effects of nicotinic antagonists with inhibition of regional brain acetylcholine synthase in rats: J Pharmacol Exp Ther Aug;258(2):403–9. (Abstract) (No Year Available).

Kalaiselvi, T. Panneerselvam, C.: Effect of L–carnitine on the status of lipid peroxidation and antioxidants in aging rats: J–nutr–biochem, New York, N.Y.: Elsevier Science Inc. Oct. 1988, v. 9 (10) p. 575–581.

Pedersen HS, Mortensen SA, Rohde M, Deguchi Y, Mulvad G, Bierregrand P, Hansen JC: High serum coenzyme Q10, positively correlated with age, selenium and cholesterol, in Inuit of Greenland. A pilot study, Biofactors 1999;9(2–4):319–23. (Abstract).

Rosenfeldt FL, Pepe S, Ou R, Mariani JA, Rowland MA, Nagley P, Linnase AW: Coenzyme Q10 improveds the tolerance of the senescent myocardium to aerobic and ischemic stress: studies in rats and in human atrial tissue, Biofactors 1999;9(2–4):291–9. (Abstract).

Kaikkonen J, Nyyssonen K, Tuomainen TP, Ristonmae U, Salonen JT: Determinants of plasma coenzyme Q10 in humans, FEBS Lett 1999 Jan 25;443(2):163–6. (Abstract).

Linnane AW, Kovalenko S, Gingold EB:The universality of bioenergetic disease. Age–associated cellular bioenergetic degradation and amerlioration therapy, Ann N Y Acad Sci 1998 Nov. 20;854:202–13.

Formiggini G, Marchetti M, Castelli GP, Bovina C: Oxidative stress, antioxidant defense and aging, Biofactors 1998:8(3–4):195–204. (Abstract).

Barbirolli B, Lotti S, Lodi R: Aspects of human bioenerbetics as studied in vivo by magnetic resonance spectroscopy, Biochimie 1998 Oct;80(10):847–53. (Abstract).

Lass A, Kwong L, Sohal RS: Mitochrondial coenzyme Q content and aging, Biofactors 1999;9(2–4):199–205. (Abstract).

Lonnrot K, Porsti I, Alho H, Wu X, Hervonen A, Tolvanen JP: Control of arterial tone after long–term coenzyme Q10 supplemation in senescent rats, Br J Pharmacol 1998 Aug;124(7):1500–6. (Abstract).

Lonnrot K, Holm P, Lagerstedt A, Huhtala H, Alho H: The effects of lifelong ubiquinone Q10 supplementation on the Q9 and Q10 tissue concentration and life span of male rats and mice: Biochrm Mol Biol Int 1998 Apr;44(4):727–37. (Abstract).

Beal MF, Matthews RT, Matthews RT, Tieleman A, Shults CW: Coenzyme Q10 attenuates the 1–methyl–4–phenyl–1, 2,3, tetrahydropyridine (MPRTP) induced loss of striatal dopamine and dopaminergic axons in aged mice, Brain Res 1998 Feb. 2;783(1):109–14. (Abstract).

Aejmelaeus R, Metsa–Ketela T, Laippala P, Solakivi T, Alho H: Ubiquinol–10 and total peroxyl radical trapping capacity of LDL lipoproteins during aging: the effects of Q10 supplementation, Mol Aspects Med 1997;18 Sepple:S113–20. (Abstract).

Pastoris O, Boschi F, Verri M, Baiardi P, Felzani G, Vecchiet J, Dossena M, Catapano M: The effects of aging on enzyme activities and metabolite concentrations in skeletal muscle from sedentary male and female subjects, Exp Gerontol 2000 Feb. 1;35(1):95–104. (Abstract).

Rawson ES, Clarkson PM: Acute creatine supplementation in older men, Int J Sports Med 2000 Jan:21(1):71–5, (Abstract).

Schuff N, Amend DL, Knowlton R, Norman D, Fein G, Weiner MW: Neurobiol Aging 1999 May–Jun.;20(3):279–85. (Abstract).

Pfefferbaum A, Adalsteinsson E, Spielman D, Sullivan EV, Lim KO: In vivo spectroscopic quantification of the N–acetyl moiety, creatine, ad choline from large vols. of brain gray and white matter: effects of normal aging, Magn Reson Med 1999 Feb;41(2):276–84,. (Abstract).

Pfefferbaum A, Adalsteinsson E, Spielman D, Sullivan EV, Lim KO: In vivo bain concentrations of N–acetyl compounds, creatine, and choline in Alzheimer disease, Arch Gen Psychiatry 1999 Feb;46(2):185–92. (Abstract).

Bermon S, Venembre P, Sachet C, Valour S, Dolisi C: Effects of creatine monohydrate ingesttion in sedentary and weight–trained older adults, Acta Physiol Scand 1998 Oct;164(2):147–55. (Abstract).

Smith SA, Montain SJ, Matott RP, Zientara GP, Jolesz FA, Fielding RA: Creatine supplementation and age influence muscle metabolism during exercise, J Appl Physiol 1998 Oct;85(4):1349–56. (Abstract).

Pastoris O, Dossena M, Arnaboldi R, Gorini A, Villa RF: Age–related alterations of skeletal muscle metabolism by intermittent hypoxia and TRH–analogue treatment, Pharmacol Res 1994 Aug.–Sep.;30(2):171–85. (Abstract).

Sobreira C, hirano M, Shanske S, Keller RK, Haller RG, Davidson E, Santorelli FM, Miranda AF, Bonilla E, Mojon DS, Barreira AA, King MP, DiMauro Mitochondrial encephalomyopathy with coenzyme Q10 deficiency: Neurology, 1997 May;48(5):1238–43. (Abstract).

Langsjoen PH, Vadhanavikit S, Folkers K: Response of patients in classes III and IV of cardiomyopathy to therapy in a blind and crossover trial with coenzyme Q10: Proc Natl Acad Sci USA, 1985 Jun.;82. (Abstract).

Langsjoen PH, Langsjoen A, Willis R, Folkers K: Treatment of hypertrophic cardiomyopathy with coenzyme Q10: Mol Aspects Med, 1997;18 Suppl:S145–51. (Abstract).

Kenneth B. Beckman and Bruce N. Ames: The Free Radical Theory of Aging Matures: Physiological Reviews, vol. 78 No. 2, Apr. 1998.

Nyberg L, Blackman L, Ernrund K, Olofsson U, Nilsson LG: Age differences in episodic memory, semantic memory, and priming: relationships to demographic, intellectual, and biological factors: J Gerontol BP Psychol Sci Soc, 1996 Jul.;51(4):P23–40. (Abstract).

Fletcher PC, Dolan RJ, Frith CD: The functional anatomy of memory: Experientia, 1995 Dec. 18:51(12): 1197–207. (Abstract).

Fletcher PC, Frith CD, Grasby PM, Shallice T, Frackowiak RS, Dolan RJ: Brain systems for encoding and retreval of auditory–verbal memory. An in vivo study in humans. Brain 1995 Apr.;118 (Pt 2):401–16. (Abstract).

Rapp PR, Heindel WC: Memory systems in normal and pathological aging: Curr Opin Neurol, 1994 Aug.;7(4):294. (Abstract).

Grasby PM, Frith CD, Friston K, Frackowiak RS, Dolan RJ: Activation of he human hippocampal formation during auditory–verbal long–term memory function: Neursci Lett, 1993 Dec. 12:163(2):185–8. (Abstract).

Heiss WD, Pawlik G, Holthoff V, Kessler J, Szelies B: PET correlates of normal and impaired memory functions: Cerebrovasc Brain Metab Rev, 1992 Spring;4(1):1–27. (Abstract).

Derouesne C: Neuropsychological testing for evaluation of brain aging: Ann Med Interne )(Paris) 1990 141 Suppl 1:27–30. (Abstract).

Haxby JV, Grady CL, Duara R, Robertson–Tchabo EA, Koziarz B, Cutler NR, Rapoport SI: Relations among age, visual memory, and resting cerebral metabolism in 40 healthy men: Brain Cogn, 1986 Oct.:5(4):412–27. (Abstract).

Riege WH, Metter EJ, Kuhl DE, Phelps ME: Brain glucose metabolism functions: age decrease factor scores: J Gerontol, 1985 Jul.;40(4):412–27. (Abstract).

Shawn D. Gale, Ramona O. Hopkins, Lindell K. Weaver, Erin D. Bigler, Edgar J. Booth and Duane D. Blatter: MRI, Quantitative MRI SPECT, and neuropsychological findings following carbon monoxide poisoning: Brain Injury, 1999 vol. 13, No. 4, 229–243,. (Abstract).

Jae–Yeon Jang, Soon Young Lee, Jae Ill Kim, Jae Beom Park, Kyung Jong Lee, Ho Keun Chung: Application of biological monitoring to the quantitative exposure assessment for neuropsychological effect by chronic exposure to organic solvents: Int Arch Occup Environ Health: 1999 72:: 107–114. (Abstract).

Jill Brooks, PhD, Lori A. Fos, BS, Kebin W. Greve, PhD, and Jeffrey S. Hammond, MD, MPH: Assessment of Executive Function in Patients with Mild Trauatic Brain Injury: The Journal of Trauma: Injury, Infection, and Critical Care, 1999 vol. 46, No. 1. (Abstract).

METHOD OF TREATING BENIGN
FORGETFULNESS

This Application claims benefit under 35USC119(e) from U.S. provisional Application No. 60/163,352 filed Nov. 3, 1999 and U.S. Provisional application No. 60/223,167 filed Aug. 7, 2000.

TECHNICAL FIELD

This invention is related to the prevention and amelioration of memory deficits related to aging and other causes. More specifically, this invention is related to the administration of micronutrients, such as an antioxidant, a canitine product, and optionally coenzyme Q and/or creatine to those at risk of memory loss.

BACKGROUND OF INVENTION

Many adults gradually develop noticeable difficulties in memory, at first for names, then for events, and sometimes even occasionally for spatial relationships. The majority of healthy older people complain about forgetfulness and decreased concentration, and this compromises their quality of life. It is well established that virtually all aspects of cognitive functioning deteriorate with age. There has also been a rapid increase in the interest of clinicians, researchers and the pharmaceutical industry in the development of new classes of drugs for the palliative treatment of age-related cognitive deficits and dementing conditions. This widely experienced so-called benign forgetfulness, or benign senescent forgetfulness, bears no proven relationship to degenerative dementia but may be a forewarning, since there are some similarities.

Kral was the first to introduce diagnostic terminology for age-associated changes in memory (J Gerontol 13: 169–176, 1958; Can Med Assoc J 86: 257–260, 1962). He used the term "benign senescent forgetfulness" (BSF) to distinguish subjects with mild memory decline from those with more severe, "malignant" changes (MSF), and also from those with normal memory functions.

Since then BSF and MSF have often been used in the medical literature and have become a generally accepted notion among clinicians. Generally, BSF is characterized by patchy and variable difficulties remembering details of experiences (names and places), but with relative ease in recalling the experience itself. Usually the forgotten details are recalled later. BSF is not progressive and does not increase the risk of developing dementia. MSF is characterized by an inability of the individual to recall events in the recent past, disorientation with regard to personal data, and retrogressive loss of remote memories. MSF individuals often are unaware of their deficit and may confabulate. In a four-year study of 20 cases of BSF and 34 of MSF, one patient with BSF deteriorated cognitively and all MSF patients deteriorated. A recent three-year study of 68 BSF patients reported that 9% became demented.

Because Kral did not operationalize the concept of BSF, a National Institute of Mental Health (NIMH) working group, which was set up to describe memory changes more precisely, proposed the concept of "age-associated memory impairment" (AAMI) as a diagnostic entity (Crook et al. 1986, ibid.). In brief, the criteria of AAMI include the presence of subjective memory decline, objective evidence of memory loss (in a well-standardized memory test, a score at least one standard deviation below the mean of younger adults), adequate intellectual function, and the absence of dementia or other memory-affecting disease (e.g. stroke) in a person aged 50 years or older. Thus, the AAMI diagnosis identifies persons with subjectively and objectively evidenced memory loss without cognitive decline impairing enough to warrant the diagnosis of dementia. The criteria leave open the question of progression in the condition.

McEntee and Crook (Neurology 40: 526–530, 1990) estimated that AAMI might affect most of the over-50 population to some degree. However, Lane and Snowdon (Memory and dementia: A longitudinal survey of suburban elderly. In: Lovibond P, Wilson P (eds). Clinical and abnormal psychology. Elsevier, Amsterdam, 365–376, 1989) reported a prevalence rate of 35% for AAMI in subjects aged 65 years or over. The results are somewhat hampered by the low participation rate (58%) of the study population, and by the fact that the methodology used did not strictly follow the definitions of the NIMH working group. On the basis of memory test performance alone, Larrabee and Crook (Int Psychogeriatr 6: 95–104, 1994) estimated the prevalence of AAMI to vary from 39% in the age group 50 to 59 years to 85% in the age group over 80 years. In that study, no exclusion criteria were employed. Barker et al. (Br J Psychiatry 167: 642–648, 1995) identified as many as 79% of the participants in the AAMI category by memory test results. However, after applying stringent exclusion criteria, they reported a 15.8% prevalence of AAMI in 50- to 64-year-old and 24.1% in 65- to 79-year-old subjects.

A task force of the International Psychogeriatric Association (IPA) in collaboration with the World Health Organization (WHO) recently proposed diagnostic criteria for "aging-associated cognitive decline" (AACD) (Levy, Int Psychogeriatr 6: 63–68, 1994). The diagnosis of AACD is based on a more comprehensive evaluation of cognition than that of AAMI. Deterioration in any major cognitive domain is sufficient for identifying AACD. The cognitive domains specified in the AACD criteria are memory and learning, attention and concentration, thinking, language and visuospatial functioning. Also differing from the AAMI criteria, the subject with AACD is required to score one standard deviation below age- and education-specific standards (not those of younger adults) in tests assessing cognitive abilities. Thus, the AACD diagnosis identifies persons with subjective and objective cognitive decline, which is not impairing enough to warrant the diagnosis of dementia. In presenting the AACD criteria, the task force recognized the individual in progression or not to dementia.

AAMI may start in middle age (around the age of 40 years), as measured by some categories of cognitive tests. Age-related cognitive problems may lie dormant for decades and only become gradually or suddenly apparent as the individual realizes that some aspect of functioning is no longer what it used to be. Some propose that gradual cognitive decline may be due to accumulation of minor brain insults, such as falls from which an individual appears to completely recover. At first, these minor pathologies may have little impact but, as they accumulate with advancing age, their amassed effects result in discernible cognitive deficits. A decline in sensory, perceptual and physical performance can greatly impact general cognitive functions, even without direct or causal relation to cognitive performance. "Executive function" appears an important mediator of age-related dysfunction, as it has been shown that after correction for executive function, age was not a predictor for test performance.

Because of the high rate of memory impairment, AAMI is likely to be a phenomenon of normal aging rather than a continuum from normal aging to a pathologic state such as Alzheimer's disease. The neuropsychological methods used for AAMI diagnosis are ambiguous and do not always differentiate subjects with very early dementia. However, these subjects can be differentiated by means of a more detailed neuropsychological evaluation. In comparison with age-matched controls, AAMI subjects appeared to be impaired not only in tests assessing memory, but also in tests of the executive finctions associated with frontal lobe finction. This finding agrees with previous reports suggesting an important role for frontal lobe dysflnction in the memory loss of elderly people. Comparing subjects with high and low frequencies of subjective complaints of memory loss suggested that these subjective feelings of memory impairment are more closely associated with personality traits than with actual memory performance in normal elderly people. This complicates the use of memory complaints in the inclusion criteria for AAMI and AACD diagnosis.

The prevalence of AACD has been found to be lower than that of AAMI. As AAMI tends to identify a very heterogeneous subject group, the AACD diagnosis might prove superior to AAMI for differentiating a meaningful subgroup from the elderly population, both for research purposes and in clinical settings. This remains to be confirmed in follow-up studies.

Prominent changes occur in the brain during aging and include a decrease in brain weight, gyral atrophy, ventricular dilation, and selective loss of neurons within different brain regions (Kemper, Neuroanatomical and neuropathological changes during aging and dementia. In: Martin A. L., Knoefel J. E. (eds). GERIATRIC NEUROLOGY (2nd ed). Oxford University Press, New York City, pp. 3–67, 1994). The relevance of these changes to behavioral measurements is still largely ambiguous (e.g., Lezak, NEUROPSYCHOLOGICAL ASSESSMENT (3rd ed). Oxford University Press, New York, 1995). In addition to biological changes, environmental contexts are reflected in age-related cognitive changes (Arbuckle et al., Psychol Aging 7: 25–36, 1992). Recent studies with advanced brain imaging methods (especially PET and functional MRI) have elucidated the neuroanatomical localization of cognitive functions (e.g., Frackowiak, Trends Neurosci 17: 109–115, 1994; Moscovitch et al., Proc Natl Acad Sci USA 92: 3721–3725, 1995; Schacter et al., Proc Natl Acad Sci USA 93: 321–325, 1996). So far, very few of these studies have considered the effects of aging (Eustache et al., Neuropsychologia 33: 867–887, 1995; Grady et al., Science 269: 218–221, 1995). However, some associations between age-related cerebral and cognitive changes have been suggested.

Eustache et al. (1995, ibid) demonstrated concomitant age-related declines in brain oxidative metabolism (in the resting condition) and tests of episodic memory, which also suggests that neurobiological changes within the neural network for episodic memory (which includes the hippocampus and the thalamus) may underlie the memory impairments of normal aging. Accordingly, Grady et al. (1995, ibid.) found age-related reductions in regional cerebral blood flow within the network including the hippocampus and the anterior cingulate cortex during the encoding phase of a face recognition task.

By using a structural equation model, Jones et al. (Exp Aging Res 17: 227–242, 1991) found evidence for a causal relationship between age-related changes in the brain (as measured by CT and EEG) and cognition in healthy individuals.

AACD and AAMI seem to overlap with various other diagnostic classifications which have been proposed (Dawe et al., Int J Geriatr Psychiatry 7: 473–479, 1992; Ebly et al., Arch Neurol 52: 612–619, 1995). The best established of these classifications are "mild cognitive disorder" (MCD) and "age-related cognitive decline" (ARCD). MCD is included in the research criteria for ICD-10 (World Health Organization 1993). This diagnosis is used only when there is an indication of a disease or condition known to cause cerebral dysfunction. The epidemiology of MCD has been considered in two recent studies with contradictory results. Christensen et al. (Age Ageing 25: 72–80, 1996) found a prevalence rate of only 4% for MCD and concluded that the diagnosis lacks validity. Ebly et al. (1995, ibid.) wanted to add the presence of subjective complaints, but otherwise agreed with the ICD-10 criteria for MCD. ARCD is included in the DSM-IV (American Psychiatric Association 1994) defined as "an objectively identified decline in cognitive functioning consequent to the aging process that is within normal limits given the person's age". However, no more detailed criteria are included in the DSM-IV, and no studies employing this construct have been conducted.

Coenzyme Q or ubiquinone plays a central role in the mitochondrial respiratory chain that captures energy from metabolism. It exists in mitochondria in the oxidized quinone form under aerobic conditions. In the reduced form ubiquinol, Q10 is an antioxidant. Q also is present in mitochondrial lipids. The structure of Q is very similar to those of vitamins K and E, which are characterized by a polyisoprenoid side chain. Coenzyme Q10 has ten polyisoprenoid side chains. Mitochondria need to maintain a large excess of Q10, compared to other respiratory enzymes. Q10 is required to act on a mobile component of respiration that collects reducing equivalents from the more fixed complexes and passes them to other compounds.

Many conflicting reports have been published on the effectiveness of Q10 in various laboratory and clinical settings. Barbiroli et al reported that Q10 administration caused marked improvement in oxidative phosphorylation in both skeletal muscles and brains of patients with mitochondrial cytopathies due to enzyme defects (Biochimie 80(10): 847–53, 1998). On the other hand, Lass et al studied the Q10 and Q9 content in brain, heart, skeletal muscle and other organs but found a decrease in mitochondrial Q9 and Q10 only in aging skeletal muscle (Biofactors 9(2–4):199–205, 1999).

Life-long Q10 supplementation was studied in male rats and mice. Q10 did not prolong or shorten the lifespan of rats or mice. Plasma and liver levels were 2.6–8.4 times higher in the supplemented rats. Q10 levels in kidney, heart and brain were not affected by Q10 supplementation (Lonnrot K et al. Biochem Mol Biol Int 44(4):727–37, 1998).

To determine if Q10 has a neuroprotective effect, mice were first treated with Q10 or a control diet for four weeks. Then their striatal nerves were poisoned 1-Me-4-Ph-1,2,3, tetrahydropyridine (MPTP). The mice continued on their assigned diets for another week before sacrifice. Both groups had considerable brain damage; however, the Q10-treated mice had 37% higher doparnine and 62% more dense neurons, indicating a protective effect of Q10. (Beal MF et al. Brain Res 783(1):109–14, 1998.

Q10 also blocks the effects of doxorubicin, which by itself stimulates mitochondrial oxidant production and a marked increase in mtDNA deletions in cardiac tissue (Adachi et al. Biochem Biophys Res Commun 195:945–51, 1993).

A group of healthy Finnish men and women aged 28–77 were tested for the total peroxyl radical-trapping capacity of human plasma LDL phospholipids. There was an age-related difference in men, but not in women. Most of the decrease occurred before age 50, remaining low into the 70's. Supplementation with Q10 doubled the peroxyl radical-trapping capacity and thus may decrease LDL oxidation, which contributes to atherosclerosis (Aejmelaeus R et al. Mol Aspects Med 18(Supp):S113–20, 1997).

Creatine is present in muscular tissue and the heart. Small amounts are found in the blood but not in normal urine. Normally the liver and kidneys produce creatine. When creatine is metabolized, its end product is creatinine, which is excreted in the urine. Serum creatinine may increase with age. Muscle mass usually decreases with age, but it is unknown if it is entirely due to declining activity with age. Also, many older people do not eat as much meat, an important source of creatine. The greater part of creatine in muscle is combined with phosphoric acid as phosphocreatine. There it plays an important part in mitochondrial metabolism. In the mitochondria, creatine kinase isoenzymes transfer high-energy phosphate to creatine. Next, creatine phosphate is transported out of the mitochondria into the cell's environment where it generates extramitochondrial ATP. Different isoenzymes of creatine kinase mediate transfer of high-energy phosphate to and from the various systems that utilize or generate it, e.g., muscle contraction and glucose metabolism.

Researchers administered creatine and have studied a number of different parameters including aging and muscle function. Acute supplementation (5 days) in men over 60 was found to have no effect in isometric strength and only small increases in isokinetic performance and body mass (Rawson E. S., Clarkson P. M., Int. J. Sports Med 21(1):71–5, 2000). Another study reported results on older adults (67–80 years, 16 females, 16 males) who were randomly assigned to control-creatine, control-placebo, trained-creatine and trained-placebo groups for an 8-week test. Both groups of trained subjects had significant increases in 1- and 12-repetitions maxima, but no beneficial effect was observed for creatine supplementation (Bermon S et al. Acta Physiol Scand 164(2):147–55, 1998). On the other hand, when a different parameter directly related to muscle metabolism was measured, a positive effect was seen after 7 days. Groups of male and female 30-year-olds and 50-year-olds performed single-leg knee-extension exercises inside an MRI. At the start of the study, the older group had lower resting phosphocreatine (PCr) and lower mean initial PCr resynthesis rate. After creatine supplementation, the resting PCr increased 15% ($P<0.05$) in the young group and 30% ($P<0.05$) in the middle-aged group. In the middle-aged group, mean initial PCr resynthesis rate increased significantly ($P<0.05$), to a level comparable to that of the young group. The time to exhaustion was increased in both groups combined after creatine supplementation. Smith SA et al. concluded that creatine supplementation has a greater effect on PCr availability and resynthesis rate in middle-aged compared with younger persons (J Appl Physiol 85(4):1349–56, 1998).

Schuff N et al. analyzed age-related metabolite change and volume loss in the hippocampus by MRI (Neurobiol Aging 29(3):279–85, May–June 1999). They analyzed N-acetyl aspartate (NAA, a neuron marker), volume changes, and ratios of NAA/choline (Cho) and NAA/Cr (creatine). Volume decreased about 20% between 36 and 85 years, while NAA/Cho decreased by 24% and NAA/Cr decreased by 26%, all of which were significant. The Cho/Cr ratio remained stable. The volume loss correlated with neuronal marker loss and indicated loss of neurons. In contrast, Pfefferbaum A et al. (Magn Reson Med 41(2):276–84, 1999) reported NAA, Cho and Cr signal densities for healthy groups of 15 young and 19 elderly persons. NAA was higher in gray than white matter but did not differ between young and old subjects, despite significant gray matter volume deficits in the older subjects. The available gray matter appeared to be intact in older healthy adults. Cr concentrations were much higher in gray than white matter and significantly higher in the older subjects. Cho concentration in gray matter was also significantly higher in older subjects. The findings in older subjects were confirmed in another study in which Pfefferbaum compared Alzheimer disease (AD) and normal aging (Arch Gen Psychiatry 56(2):185–92, 1999). Both groups showed cortical gray matter volume deficits. Gray matter NAA was reduced only in the AD group, compared to older and younger subjects. Cho levels were higher in the AD group versus the normal older group and were higher than in the young group. Gray matter creatine, phosphocreatine and choline concentrations in patients with AD correlated with poorer performance on recognition memory tests.

Nutritional deficiencies are known to contribute to memory difficulties. For example, the Wemnicke-Korsakoff syndrome results from a failure to ingest thiamine. The patient has continued carbohydrate intake and gradually exhausts thiamine stores in critical areas of the thalamus and brainstem reticular formation. Underlying causes include dialysis, oversights in postoperative care, hyperemesis gravidarum and severe alcoholism. Memory for new information is severely affected but memory of distant events is less impaired. Therefore, the patient's previous experience is available to guide his actions and he may display little intellectual loss. Properly treated with fluids, calories and vitamin supplements, the condition dissipates over a period of weeks to months. Studies have demonstrated an association between the use of thiamin (vitamin B1), pyridoxine (vitamin B6) or cyanocobalamin (vitamin B12), and cognition. These vitamins are involved in carbohydrate metabolism.

Zinc levels are known to be low in the older population and zinc blood levels have positively correlated with psychological performance.

What is needed is improved nutrition to maintain brain finction and prevent and ameliorate memory impairment.

SUMMARY OF INVENTION

It is an object of the present invention to prevent and ameliorate the cognitive deficits which occur with aging. It is an object of the present invention to prevent and ameliorate the cognitive deficits which occur in a variety of other disorders associated with impaired metabolism of the brain, including stroke, traumatic brain injury, toxic exposure and Type 2 diabetes mellitus. It is a firther object to provide a combination of an effective amount of a suitable antioxidant and an effective amount of a carnitine to prevent and/or ameliorate the cognitive deficits associated with the above conditions.

A preferred combination of the present invention includes carnitine in the amount of 0.12 grams to 3 grams. A preferred form of carnitine is acetyl-L-carnitine (ALC).

A preferred combination of the present invention includes the antioxidant as R-α-lipoic acid in the amount of about 0.12 grams to about 1.5 grams.

Optionally, coenzyme Q and/or creatine also are administered. Preferably 10 mg to 500 mg/day of coenzyme Q10 and 1 to 30 grams/day of creatine are administered.

DETAILED DESCRIPTION

Testing with PET, particularly enhanced with F-18 fluorodeoxyglucose (FDG) to analyze metabolic activity, has shown that two derived factors separated healthy persons below age 42 from those above age 48. Both secondary memory for material verbally processed in combination with Broca's metabolic ratio and tests requiring sequential or organizational coding of information (executive function) combined with metabolic measures of thalamic regions were greater for the younger group than for the older group. The investigators concluded that a frontal-subcortical decrement in metabolism is present in age-dependent memory processing. Riege W. H. et al. Brain Cogn 5(4): 412–27, 1986. Thus, it may be beneficial in the late 30's to early 40's to begin therapy which enhances metabolism and has been proven to counteract aging in mitochondria.

Carnitine and lipoic acid, and optionally coenzyme Q and/or creatine, are administered to discourage age-related memory loss and provide improved memory older individuals and others with unhealthy mitochondria. Recent research has shown precisely how these compounds work to promote healthy mitochondria, which are the energy powerhouses of the cells. Mitochondria are responsible for the production of ATP and are present in relatively high numbers in essentially all cells of the body. The mitochondrial electron transport system consumes approximately 85% of the oxygen utilized by a cell. Cellular energy deficits caused by declines in mitochondrial function can impair normal cellular activities and compromise the cell's ability to adapt to various physiological stresses, a major factor in aging. Because of this high oxygen use, the mitochondria also have the highest production of oxidants.

Oxidants damage mitochondria in three important ways. Oxidants damage DNA, lipids and protein. The intra-mitochondrial DNA (mtDNA) have levels of oxidative damage which are at least 10-fold higher than those of nuclear DNA, which correlates with the 17-fold higher evolutionary mutation rate in mtDNA compared with nuclear DNA. mtDNA oxidation accumulates as a function of age, which has been shown in several species, including humans. This may lead to dysfunctional mitochondria. Mitochondrial protein damage is also age-related and may decrease energy production and increase oxidant production. Oxidative damage to mitochondrial lipids contributes to the decreasing fluidity of cell membranes with age. The lipid cardiolipin is a major component of the mitochondrial membrane and facilitates the activities of critical mitochondrial inner membrane enzymes. The aged, damaged mitochondrial membrane cannot contain the oxidants nor can it maintain as high a polarity as the younger membrane.

Fatty acid oxidation is an important energy source for many tissues. The activity of carnitine-acetyl-carnitine exchange across the inner mitochondrial membrane is of great importance. The activity of this exchange reaction is decreased significantly with age, which may be due to a lower intra-mitochondrial pool of carnitine. L-carnitine or ALC has been shown to slow or reverse this age-related dysfunction. It also can reverse the age-related decrease in cardiolipin, age-associated decrease in mtDNA transcription, and decreased membrane potential. By itself, L-carnitine or ALC cannot correct the problem of excess oxidants. In fact, it was recently reported that carnitine supplementation increased oxidant production by 30% and decreased cell antioxidants markedly. Thus, ALC administration alone in older individuals may contribute to greater oxidative stress.

For the age-compromised mitochondrial engines to run on all cylinders, both carnitine and lipoic acid are essential. Lipoic acid is an antioxidant. And R-α-lipoic acid is a mitochondrial enzyme which can help reverse the decline in metabolism seen with age. R-α-alipoic acid supplementation has been shown to 1) reverse the age-related decrease in oxygen consumption, 2) restore the age-related decline in mitochondrial membrane potential, 3) triple the ambulatory activity of aged rats, 4) significantly lower the age-related increase in oxidants, and 5) restore glutathione and ascorbic acid levels to youthful levels.

Clearly, both carnitine and lipoic acid contribute to restoration of age-related mitochondria function and metabolic activity in individuals in which those were compromised. This contributes to improvements in energy, general health, mental acuity, immune system function, skin and hair appearance and muscle mass.

Carnitine is available in many forms and all those are included in the invention of the combination of carnitine and thioctic acid. Carnitine and carnitine derivatives have been used as metabolites in animal husbandry and for human diet and therapy. U.S. Pat. No. 5,362,753 (Method of increasing the hatchability of eggs by feeding hens carnitine); U.S. Pat. No. 4,687,782 (Nutritional composition for enhancing skeletal muscle adaptation to exercise training); U.S. Pat. No. 5,030,458 (Method for preventing diet-induced carnitine deficiency in domesticated dogs and cats); U.S. Pat. No. 5,030,657 (L-camitine supplemented catfish diet); U.S. Pat. No. 4,343,816 (Pharmaceutical composition comprising an acyl-carnitine, for treating peripheral vascular diseases); U.S. Pat. No. 5,560,928 (Nutritional and/or dietary composition and method of using the same); U.S. Pat. No. 5,504,072 (Enteral nutritional composition having balanced amino acid profile); U.S. Pat. No. 5,391,550 (Compositions of matter and methods for increasing intracellular ATP levels and physical performance levels and for increasing the rate of wound repair); U.S. Pat. No. 5,240,961 (Method of treating reduced insulin-like growth factor and bone loss associated with aging); etc. Most preferably, the carnitine is acetyl-L-carnitine.

A daily dosage of carnitine is about 10 mg to 8 g. Preferably the daily dose of carnitine is 25–1,000 mg. More preferably, the daily dose of carnitine is about 40–700 mg. Most preferably, the daily dose of carnitine is at least about 50 milligrams (0.05 g) per day.

By lipoic acid or thioctic acid is meant a mitochondrially active antioxidant which physiologically comprises a metabolically reactive thiol group. Mitochondrially active antioxidants including vitamins (especially C, E, B and D), glutathione, N-acetyl cysteine (NAC), lipoic acid, their derivatives, etc., have been used variously as human nutritional supplements and in dietary prophylaxis and therapy. For example, applications of lipoic acid have included U.S. Pat. No. 5,607,980 (Topical compositions having improved skin); U.S. Pat. No. 5,472,698 (Composition for enhancing lipid production in skin); U.S. Pat. No. 5,292,538 (Improved sustained energy and anabolic composition and method of making); U.S. Pat. No. 5,536,645 (Nutritive medium for the culture of microorganisms); U.S. Pat. No. 5,326,699 (Serum-free medium for culturing animal cells); etc. Preferably, the compound is at least one of glutathione, N-acetyl cysteine and lipoic acid. Most preferably, the compound is the Renantiomeric form of lipoic acid. Metabolites of lipoic acid have been found to have a longer half life and also are suitable for supplementation.

A daily dosage of lipoic acid is about 10 mg to 8 g. Preferably the daily dose of lipoic acid is 25–1,000 mg. More preferably, the daily dose of lipoic acid is about 40–700 mg. Most preferably, the daily dose of lipoic acid is at least about 50 milligrams (0.05 g) per day.

Q10 supplementation also is important. In groups of males and females ranging from 90–106 years, inadequate Q10 status was present in 40% for women and 24% for men. In women, the decreased Q10 was associated with impaired natural killer cell effectiveness (p<0.05), indicating decreased ability to fight infections and to quickly eliminate individual cancer cells as they first develop. Q10 also appears to block programmed cell death, or apoptosis, through its action in the mitochondria (Kagan T et al, Ann NY Acad Sci 887:31–47, 1999). Furthermore, Q10 in its reduced form of ubiquinol-10, which is normally present in the blood, appears to protect human lymphocytes from oxidative damage to DNA (Tomasetti et al, Free Radic Biol Med 27 (9–10):1027–32, Nov. 1999). No important adverse effects have been reported from experiments using daily supplements of up to 200 mg Q10 for 6–12 months and 100 mg daily for up to 6 y. Overvad K et al. Eur J Clin Nutr 53(10):764–70, 1999.

Q10 also may contribute to anti-aging effect by protecting against atherosclerosis which also results from oxidative stress. Pedersen HS, et al. Biofactors 9(2–4): 319–23, 1999). Protecting brain blood vessels will also help support brain function.

As for the appropriate dose of Q10, older Finnish men obtained benefit from 100 mg/day. A woman deficient in Q10 received 150 mg/kg and rapidly improved (Sobriera et al. Neurology 48:1283–43, 1997). Q10 has also been used at chronic doses of about 200 mg/day to improve heart function in persons with hypertrophic cardiomyopathy. Based on this information, a supplemental dosage ranges from about 10 mg/day to about 500 mg/day. Preferably, the Q10 dose is about 100 mg/day.

Because creatine is often deficient in older individuals, creatine supplementation is important. Many athletes have taken doses of creatine up to 75 grams a day for years without known adverse effects, aside from weight gain attributed to increased muscle mass. Creatine may be most beneficial when ingested with glucose, which tends to increase creatine absorption. Often athletes ingest loading doses of 20 g/day divided into four doses for 5 days to one week. Then they take a maintenance dose of 5 g/day. Benefit in one week in older individuals (40–73) has also been seen from a 20 g/day dose, in the form of increased skeletal muscle strength and endurance. It has been reported that 1.5 g–25 g/day are safe for period of at least a year. A suitable dosage range is 0.5 g/day to 25 g/day, preferably 1–10 grams per day and most preferably about 5 g/day. Creatine is available as a salt, monohydrate, phosphate and citrate.

In addition to the compositions mentioned above and the examples given below, breakfast products would also benefit from the addition of a carnitine, a form of thioctic acid, and optionally Q10 and/or creatine. Examples of such breakfast products include, but are not limited to, breakfast cereal (Total®, etc.), breakfast bars, Poptart® pastry, and quick breakfasts in a bun or taco (e.g., McDonald® Egg McMuffin®). The carnitine, thioctic acid, and optionally Q10 and/or creatine can be added to bulk powders or powder packets, for example, in the following compositions: orange juice (e.g., Tang®), coffee creamer (e.g., Cremora®), powdered milk, powdered milk shakes/ smoothies (e.g., MetaRX), butter-flavored powder, sweetener powders (e.g., Nutrasweet®), and spice and herb mixes. The combination of carnitine, thioctic acid, and optionally Q10 and/or creatine can be mixed with any cooked or uncooked food.

Premade drinks which would benefit from the inclusion of carnitine, thioctic acid, and optionally Q10 and/or creatine include, but are not limited to, pre-made smoothies, additives to drinks like Jamba Juice® and Starbucks®, sports drinks such as Gatorade®, diet drinks such as Weight Watchers® and Slim Fast®, and herbal drinks such as SoBe® (with St. John's Wort and other popular herbs). The formulations with carnitine, thioctic acid, and optionally Q10 and/or creatine also can include any fortified foods or meals replacement foods.

The combination of carnitine, thioctic acid, and optionally Q10 and/or creatine is provided in pet formulations, dried or canned or as a supplement for addition thereto. Animals expected to benefit from the composition include but are not limited to dogs, cats, horses, birds and fish.

The formulations and/or content of these products are on the product label or are otherwise publicly available.

Additional nutrients are particularly important in older individuals, including calcium, vitamins B12, B6, C, D or E, folic acid, niacin, iron and zinc. Many of these nutrients have been found to be deficient in the diets of elders and should be appropriately supplemented in nutritional beverages and bars.

A preferred formulation provides lipoic acid and carnitine, optionally in combination with coenzyme Q10 and/or creatine, in a timed release formulation to provide a steady supply of the nutrients to the mitochondria which work 24 hours a day. One method of accomplishing timed release is chemically combining the micronutrient(s) with other molecules, which generally slows the process of making the micronutrient(s) available. Also the use of different salts of the micronutrients with different dissolution rates provides for gradual and appropriate release of the product.

Besides these methods, two other basic systems are used to control release for oral administration: coating a core comprising the micronutrient(s) and excipients (coated system) and incorporating the micronutrient(s) into a matrix (matrix system). Coated systems involve the preparation of product-loaded cores and coating the cores with release rate-retarding materials. Product-loaded cores can be formulated as microspheres, granules, pellets or core tablets. There are many known core preparation methods, including, but not limited to, 1) producing granules by top spray fluidized bed granulation, or by solution/suspension/ powdering layering by Wurster coating, 2) producing spherical granules or pellets by extrusion-spheronization, rotary processing, and melt pelletization; 3) producing core tablets by compression and coating with a release rate-retarding material; 4) producing microspheres by emulsification and spray-drying.

Matrix systems embed the micronutrient in a slowly disintegrating or non-disintegrating matrix. Rate of release is controlled by the erosion of the matrix and/or by the diffusion of the micronutrient(s) through the matrix. In general, the active product substance, excipients and the release rate-retarding materials are mixed and then processed into matrix pellets or tablets. Matrix pellets can be formed by granulation, spheronization using cellulosic materials, or by melt pelletization using release retardant materials, while matrix tablets are prepared by compression in a tablet press. An example of a cellulosic material is hydroxypropylmethylcellulose as the release rate-retarding material.

Coated or matrix pellets can be filled into capsules or compression tabletted. The rate of release can be futrther modified by blending coated or matrix pellets with different release rates of the same product to obtain the desired product release profile. Pellets containing any of lipoic acid, carnitine, coenzyme Q10 or creatine can be blended to form a combination product. Convenient assays for the requisite bioactivities are described above or in the references cited herein. For example, cardiolipin content is readily assayed as referenced in Guan, Z. Z., Soderberg, M., Sindelar, P., and Edlund, C. Content and Fatty Acid Composition of Cardiolipin in the Brain of Patients with Alzheimer's Disease. Neurochem. Int. 25: 295–300, 1994 and oxidant production (DCFH) may be assayed as described by LeBel, C. P., Ischiropoulos, H., and Bondy, S. C. Evaluation of the Probe 2',7'-Dichlorofluorescein as an Indicator of Reactive Oxygen Species Formation and Oxidative Stress. Chem. Res. Toxicol. 5: 227–231, 1992. Assays for parameters of memory loss associated with aging and other activities such as host activity and behavior such as grooming, sexual activity, dominance are similarly well known in the art.

Testing for AAMI or other memory deficits can be performed with the Mini-Mental Status Examination, which provides a numerical score within about 5–10 minutes. As a quick screen, simply assessing orientation and asking the patient to draw a clock with the hands at a set time (e.g., 10 min before 2:00) can be very informative regarding cognitive status, visuospatial deficits, ability to comprehend and execute instructions in logical sequence, and presence or absence of perseveration.

PET scans and functional MRI can localize and quantitate the neuroanatomical localization of cognitive deficits (e.g., Frackowiak. Trends Neurosci 17: 109–115, 1994; Moscovitch et al. Proc Natl Acad Sci USA 92: 3721–3725, 1995; Schacter et al. Proc Natl Acad Sci USA 93: 321–325, 1996). Some studies have documented the effects of aging (Eustache et al. Neuropsychologia 33: 867–887, 1995; Grady et al. Science 269: 218–221, 1995).

EXAMPLE Carbon Monoxide Poisoning

Carbon monoxide (CO) poisoning causes cognitive impairments due to anoxia and other related biochemical mechanisms. In 21 patients with CO poisoning, brain-behavior relationships, neuropsychological outcome, SPECT, MRI, and Quantitative MRI (QMRI) were studied. Ninety-three per cent of the patients exhibited a variety of cognitive impairments, including impaired attention, memory, executive function, and mental processing speed. Imaging studies revealed that 67% had QMRI findings including hippocampal atrophy and/or diffluse cortical atrophy evidenced by an enlarged ventricle-to-brain ratio (VBR). Cerebral perfusion defects included frontal and temporal lobe hypoperfiusion (Gale SD et al. *Brain Inj* 13(4):229–43, 1999).

Treatment of such patients includes administration of a combination of carnitine, thioctic acid, and optionally Q10 and/or creatine to support the mitochondria. Such therapy preferably begins immediately after the discovery of the poisoning to ameliorate the drastic effects of anoxia on the brain.

EXAMPLE Type 2 Diabetes Mellitus (DM)

Type 2 DM has been associated with cognitive impairment, probably both for memory and executive function. There is also evidence for an elevated risk of both vascular dementia and Alzheimer's disease in Type 2 DM, in spite of strong interaction with other factors such as hypertension, dyslipidemia and apolipoprotein E phenotype. Further research into the mechanisms of cognitive impairment in Type 2 DM may allow scientists to challenge the concept of dementia, at least in these patients, as an irremediable disease. (Stewart R and Liolitsa D. *Diabet Med* 16(2):93–112, 1999).

This impairment in memory and executive function is similar to that seen in age-related memory deficits and thus is susceptible to treatment with a combination of carnitine, thioctic acid, and optionally Q10 and/or creatine to support the mitochondria, which also are compromised in Type 2 DM.

EXAMPLE Obsessive-Compulsive Disorder

Previous neuropsychological studies of obsessive-compulsive disorder (OCD) have indicated impaired executive functioning and nonverbal memory. A recent study investigated the mediating effects of organizational strategies used when copying a figure on subsequent nonverbal memory for that figure. Neuropsychological performance in 20 unmedicated subjects with OCD was compared with 20 matched normal control subjects. Subjects were administered the Rey-Osterrieth Complex Figure Test (RCFT) and neuropsychological tests assessing various aspects of executive function. OCD subjects differed significantly from healthy control subjects in the organizational strategies used to copy the RCFT figure, and they recalled significantly less information on both immediate and delayed testing. Multiple regression analyses indicated that group differences in immediate percent recall were significantly mediated by copy organizational strategies. Further exploratory analyses indicated that organizational problems in OCD may be related to difficulties shifting mental and/or spatial set. Immediate nonverbal memory problems in OCD subjects were mediated by impaired organizational strategies used during the initial copy of the RCFT figure. Thus, the primary deficit was in executive fuinction, which then had a secondary effect on immediate memory. These findings are consistent with current theories proposing frontal-striatal system dysfunction in OCD. (Savage C. R. et al. *Biol Psychiatry* 45(7):905–16, 1999).

A similar frontal-striatal system is affected in age-related memory deficits and a similar treatment can be used in OCD, namely, administration of carnitine, thioctic acid, and optionally Q10 and/or creatine.

EXAMPLE Environmental Toxin Exposure

In workers at a shipyard, environmental monitoring and biological monitoring were performed to evaluate the effects of chronic exposure to organic solvents. Cumulative exposure (CE) and lifetime-weighted average exposure variables were developed with both environmental and biological monitoring data. A neuropsychological questionnaire and a function test for confirmation of a disorder or dysfunction in attention, executive function, visuospatial, and constructional abilities, learning and memory, and psychomotor function were performed. In the exposed group, the abnormal rate in neuropsychological diagnosis was 9.3%. This was much higher than the 2.1% rate obtained in the non-exposed workers (P<0.01). (Jang J. Y. et al. *Int Arch Occup Environ Health* 72(2):107–14, 1999)

Individuals who may be exposed to organic solvents or other environmental toxins are clearly at risk for developing memory deficits similar to those seen in older individuals. Individuals exposed to environmental toxins would be well served to take carnitine, thioctic acid, and optionally Q10 and/or creatine as a way to preserve their mitochondria and the mitochondria's ability to deal with metabolites, such as oxidants.

EXAMPLE Mild Traumatic Brain Injury

A recent study used several neuropsychological tests to identify sequelae of mild traumatic brain injury (TBI). Eleven adult patients who had experienced mild TBI were administered the following tests: the Wechsler Intelligence Scale for Children-Revised: Mazes Subtest, Trails A and B, the Boston Naming Test, The Multilingual Aphasia Examination: Controlled Oral Word Association Test, and the Paced Auditory Serial Addition Task. Control subjects performed significantly better than patients with mild TBI on Trails A and B, the Controlled Oral Word Association Test, and Paced Auditory Serial Addition Task (subtests 2–4). No significant differences in performances between TBI patients and controls were found for the Wechsler Intelligence Scale for Children -Revised: Mazes Subtest, Boston Naming Test, and Paced Auditory Serial Addition Task Subtest 1. The results suggest that patients who have had even mild TBI have abnormal executive function. (Brooks J et al. *J Trauma* 46(1):159–63, 1999).

Patients with mild TBI have an initial deficit similar to that of persons with age-related memory loss and also can benefit from the administration of a combination of carnitine, thioctic acid, and optionally Q10 and/or creatine to help them recover from an injury which will tax the ability of mitochondria to generate sufficient energy and to control dangerous oxidants.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method of treating age-related memory deficits, the method comprising administering effective amounts of a suitable antioxidant, a carnitine and optionally coenzyme Q and/or creatine.

2. The method of claim 1 wherein the carnitine administered is ALC and the effective amount is about 0.025 grams/day to about 3 grams/day.

3. The method of claim 1 wherein the antioxidant administered is R-α-lipoic acid.

4. The method of claim 1 wherein the antioxidant is administered in the amount of about 0.025 grams/day to about 1.5 grams/day.

5. The method of claim 1 wherein the coenzyme Q is coenzyme Q10 and is administered in the amount of about 10 mg/day to about 500 mg/day.

6. The method of claim 1 wherein the creatine is administered in the amount of about 1 gram/day to about 30 grams/day.

7. A method of treating Mild Traumatic Brain Injury, the method comprising administering effective amounts of a suitable antioxidant, a carnitine and optionally coenzyme Q and/or creatine.

8. The method of claim 7 wherein the carnitine administered is ALC and the effective amount is about 0.025 grams/day to about 3 grams/day.

9. The method of claim 7 wherein the antioxidant administered is R-α-lipoic acid.

10. The method of claim 7 wherein the antioxidant is administered in the amount of about 0.025 grams/day to about 1.5 grams/day.

11. The method of claim 7 wherein the coenzyme Q is coenzyme Q10 and is administered in the amount of about 10 mg/day to about 500 mg/day.

12. The method of claim 7 wherein the creatine is administered in the amount of about 1 gram/day to about 30 grams/day.

13. A method of treating Carbon Monoxide poisoning, the method comprising administering effective amounts of a suitable antioxidant, a carnitine and optionally coenzyme Q and/or creatine.

14. The method of claim 9 wherein the carnitine administered is ALC and the effective amount is about 0.025 grams/day to about 3 grams/day.

15. The method of claim 13 wherein the antioxidant administered is R-α-lipoic acid.

16. The method of claim 13 wherein the antioxidant is administered in the amount of about 0.025 grams/day to about 1.5 grams/day.

17. The method of claim 13 wherein the coenzyme Q is coenzyme Q10 and is administered in the amount of about 10 mg/day to about 500 mg/day.

18. The method of claim 13 wherein the creatine is administered in the amount of about 1 gram/day to about 30 grams/day.

19. A method of treating memory deficits associated with Type 2 Diabetes Mellitus (DM), the method comprising administering effective amounts of a suitable antioxidant, a carnitine and optionally coenzyme Q and/or creatine.

20. The method of claim 19 wherein the carnitine administered is ALC and the effective amount is about 0.025 grams/day to about 3 grams/day.

21. The method of claim 19 wherein the antioxidant administered is R-α-lipoic acid.

22. The method of claim 19 wherein the antioxidant is administered in the amount of about 0.025 grams/day to about 1.5 grams/day.

23. The method of claim 19 wherein the coenzyme Q is coenzyme Q10 and is administered in the amount of about 10 mg/day to about 500 mg/day.

24. The method of claim 19 wherein the creatine is administered in the amount of about 1 gram/day to about 30 grams/day.

25. A method of treating memory deficits associated with Obsessive-Compulsive Disorder, the method comprising administering effective amounts of a suitable antioxidant, a carnitine and optionally coenzyme Q and/or creatine.

26. The method of claim 25 wherein the carnitine administered is ALC and the effective amount is about 0.025 grams/day to about 3 grams/day.

27. The method of claim 26 wherein the antioxidant administered is R-α-lipoic acid.

28. The method of claim 26 wherein the antioxidant is administered in the amount of about 0.025 grams/day to about 1.5 grams/day.

29. The method of claim 13 wherein the coenzyme Q is coenzyme Q10 and is administered in the amount of about 10 mg/day to about 500 mg/day.

30. The method of claim 13 wherein the creatine is administered in the amount of about 1 gram/day to about 30 grams/day.

31. A method of treating memory deficits associated with Environmental Toxin Exposure, the method comprising administering effective amounts of a suitable antioxidant, a carnitine and optionally coenzyme Q and/or creatine.

32. The method of claim 31 wherein the carnitine administered is ALC and the effective amount is about 0.025 grams/day to about 3 grams/day.

33. The method of claim 31 wherein the antioxidant administered is R-α-lipoic acid.

34. The method of claim 31 wherein the antioxidant is administered in the amount of about 0.025 grams/day to about 1.5 grams/day.

35. The method of claim 31 wherein the coenzyme Q is coenzyme Q10 and is administered in the amount of about 10 mg/day to about 500 mg/day.

36. The method of claim 31 wherein the creatine is administered in the amount of about 1 gram/day to about 30 grams/day.

* * * * *

UNITED STATES PATENT AND TRADEMARK OFFICE
CERTIFICATE OF CORRECTION

PATENT NO. : 6,335,361 B1
DATED : January 1, 2002
INVENTOR(S) : Hamilton

It is certified that error appears in the above-identified patent and that said Letters Patent is hereby corrected as shown below:

Title page,
Item [57], ABSTRACT,
Line 4, please replace "oxidant. Preferably the oxidant" with
-- antioxidant. Preferably the antioxidant --

Column 2,
Line 35, please replace "leaming" with -- learning --
Line 42, please replace "impairing" with -- impaired --

Column 3,
Line 7, please replace "finc" with -- func --
Line 9, please replace "dysfinction" with -- dysfunction --

Column 4,
Line 57, please replace "doparnine" with -- dopamine --

Column 6,
Line 20, please replace "Wemnicke" with -- Wernicke --
Line 33, please replace "thiamin" with -- thiamine --
Line 50, please replace "firther" with -- further --

Column 8,
Line 60, please replace "Renantiomeric" with -- R-enantiomeric --

Column 9,
Line 57, please replace "camitine" with -- carnitine --

Column 10,
Line 65, please replace "futrther" with -- further --

UNITED STATES PATENT AND TRADEMARK OFFICE
CERTIFICATE OF CORRECTION

PATENT NO.    : 6,335,361 B1
DATED         : January 1, 2002
INVENTOR(S)   : Hamilton It is certified that error appears in the above-identified patent and that said Letters Patent is hereby corrected as shown below:

<u>Column 11,</u>
Line 50, please replace "hypoperfiusion" with -- hypoperfusion --

<u>Column 12,</u>
Line 34, please replace "fuinction" with -- function --

Signed and Sealed this

Twenty-eighth Day of January, 2003

JAMES E. ROGAN
*Director of the United States Patent and Trademark Office*